United States Patent [19]

Michaelis

[11] Patent Number: 5,922,904
[45] Date of Patent: Jul. 13, 1999

[54] BULK DYEING USING QUINOPHTHALONE DYESTUFFS

[75] Inventor: Stephan Michaelis, Odenthal, Germany

[73] Assignee: Bayer Aktiengesellschaft, Leverkusen, Germany

[21] Appl. No.: 09/153,201

[22] Filed: Sep. 15, 1998

Related U.S. Application Data

[62] Division of application No. 09/013,831, Jan. 27, 1998, which is a division of application No. 08/826,961, Apr. 9, 1997, Pat. No. 5,800,573, which is a continuation-in-part of application No. 08/711,141, Sep. 9, 1996, abandoned, which is a continuation of application No. 08/536,551, Sep. 29, 1995, abandoned.

[30] Foreign Application Priority Data

Oct. 6, 1994 [DE] Germany .................. 44 35 714

[51] Int. Cl.⁶ ........................................ C07C 59/76
[52] U.S. Cl. .............................................. 562/460
[58] Field of Search .................................. 562/460

[56] References Cited

U.S. PATENT DOCUMENTS

| 4,235,787 | 11/1980 | Schulz et al. | 562/410 |
| 5,037,799 | 8/1991 | Chapman et al. | 503/227 |

FOREIGN PATENT DOCUMENTS

| 0705885A1 | 4/1996 | European Pat. Off. . | |
| 2143942 | 2/1973 | France . | |
| 1569672 | 1/1971 | Germany . | |
| 02187470 | 6/1991 | Japan . | |
| 1386846 | 3/1975 | United Kingdom . | |

OTHER PUBLICATIONS

Abstract (WPAT) 84–237836/39 of DE 1569672A (Jan. 21, 1971).
Chemical Abstracts, vol. 86, No. 12, abstract No. 74331f, p. 86 (1977) Abstract of JP 7692371.
Derwent Abstracts, Abstract No. 35055U/25, abstract of JP 51092371 (Aug. 13, 1976).
Derwent Abstracts, Abstract No. 86–098703/15, abstract of JP 61044956 (Mar. 4, 1986).

*Primary Examiner*—Zinna Northington Davis
*Attorney, Agent, or Firm*—Sprung Kramer Schaefer & Briscoe

[57] ABSTRACT

Benzoyl phthalic acids of the formula

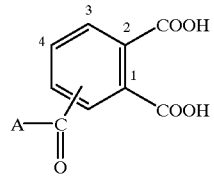

useful as intermediates in the preparation of quinophthalone dyestuffs.

3 Claims, No Drawings

BULK DYEING USING QUINOPHTHALONE DYESTUFFS

This application is a division of application Ser. No. 09/013,831, filed on Jan. 27, 1998, now allowed; which is a division of application Ser. No. 08/826,961, filed on Apr. 9, 1997, now U.S. Pat. No. 5,800,573; which is a continuation-in-part of application Ser. No. 08/711,141, filed on Sep. 9, 1996, now abandoned which is a continuation of application Ser. No. 08/536,551, filed on Sep. 29, 1995 now abandoned.

The invention relates to a process for the bulk dyeing of plastics using quinophthalone dyestuffs, and to new quinophthalone dyestuffs.

Quinophthalone dyestuffs are already known from DE-A 15 69 672 for dyeing textile materials, from U.S. Pat. No. 5,037,799 for thermal transfer printing and from JP-A-61 44 956 for dyeing liquid crystal compositions. Individual quinophthalone dyestuffs have also been described for the bulk dyeing of plastics. Such dyestuffs are mentioned, for example, in DE-A 21 32 681 and DE-A 22 03 348 in the form of compounds in which the hydroxyquinaldine radical is halogenated in the 4-position. However, these compounds have an inadequate heat stability for the use on which this invention is based. Further quinophthalone dyestuffs are known, for example, from JP-A-18 74 70 and JP-A-51/092 371.

A process has now been found for the bulk dyeing of plastics, which is characterized in that a dyestuff of the formula (I)

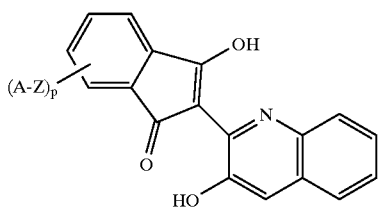

(I)

wherein
Z represents $SO_2$ or CO,
A represents alkyl, in particular $C_1$–$C_{10}$-alkyl, or aryl, in particular $C_6$–$C_{10}$-aryl, each of which is unsubstituted or substituted by halogen, $C_1$–$C_4$-alkylmercapto, cyano, $C_1$–$C_4$-alkylcarbamino, $C_6$–$C_{10}$-aryl, $C_6$–$C_{10}$-aryloxy or $C_1$–$C_4$-alkoxy and
p denotes 1 or 2,
is used.

The above process in which those dyestuffs of the formula (I) wherein A represents $C_6$–$C_{10}$-aryl, in particular phenyl or naphthyl, which is unsubstituted or substituted by halogen, in particular chlorine, bromine and fluorine, $C_1$–$C_4$-alkyl, such as methyl, ethyl, n-propyl, isopropyl, n-butyl and tert-butyl, cyano, $C_1$–$C_4$-alkylcarbamino, phenyl, phenoxy or $C_1$–$C_4$-alkoxy, in particular methoxy and ethoxy, are used is preferred. These substituents moreover are also preferred if A denotes a substituted $C_1$–$C_{10}$-alkyl.

In a preferred embodiment, p represents 1.
In a particularly preferred embodiment Z represents CO.
Preferred arylcarbonyl radicals formed from A and Z together are, for example: benzoyl, 2-, 3- and 4-chlorobenzoyl, 2-, 3- and 4-methylbenzoyl, 4-methoxybenzoyl, 4-ethoxybenzoyl, 2,3-dichlorobenzoyl, 3,5-dimethylbenzoyl, 4-phenyl-benzoyl, 1-naphthoyl, 2-naphthoyl and 2-methoxy-1-naphthoyl.

The arylsulphonyl radicals preferably formed from A and Z together are, for example: benzenesulphonyl, 4-methylbenzenesulphonyl, 4-methoxybenzenesulphonyl, 4-isopropylbenzenesulphonyl, 2- or 4-chlorobenzenesulphonyl, 2,4-dichlorobenzene-sulphonyl, 4-methylmercaptobenzenesulphonyl, 4-acetaminobenzenesulphonyl, 1-naphthalenesulphonyl, 2-naphthalenesulphonyl.

Dyestuffs of the formula (I) in which A and Z together form an optionally substituted benzoyl or benzenesulphonyl radical, in particular those which correspond to the formula (II) or (III)

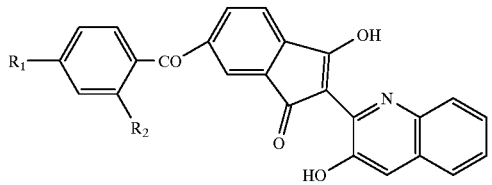

(II)

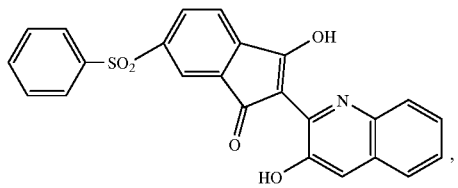

(III)

wherein
$R^1$ and $R^2$ independently of one another denote hydrogen or methyl, are particularly preferably used in the above process.

The invention also relates to dyestuffs of the formula (I)

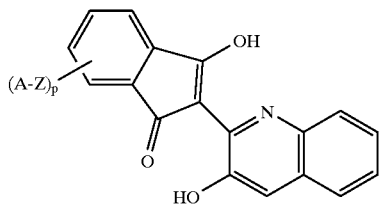

(I)

wherein
Z represents $SO_2$,
A represents aryl, which is unsubstituted or substituted by halogen, $C_1$–$C_4$-alkyl, $C_1$–$C_4$-alkylmercapto, cyano, $C_1$–$C_4$-alkylcarbamino, $C_6$–$C_{10}$-aryl, $C_6$–$C_{10}$-aryloxy or $C_1$–$C_4$-alkoxy, and
p denotes 1 or 2.

The invention also relates to dyestuffs of the formula (I) that corresponds to formula (Ia)

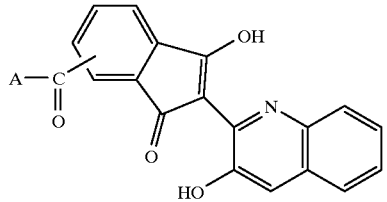

(Ia)

wherein

A represents a radical selected from the group consisting of

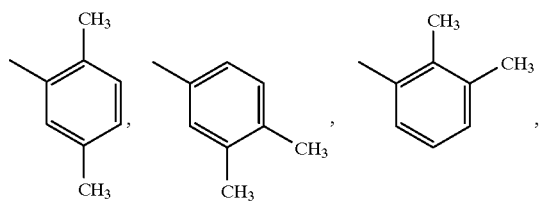

and

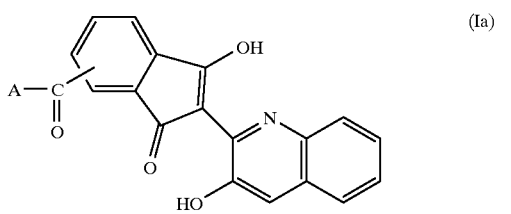

The invention also relates to a process for the preparation of dyestuffs of the formula (Ia),

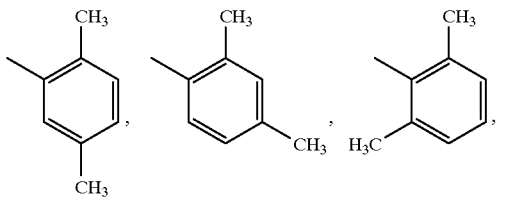

(Ia)

wherein

A represents a radical selected from the group consisting of

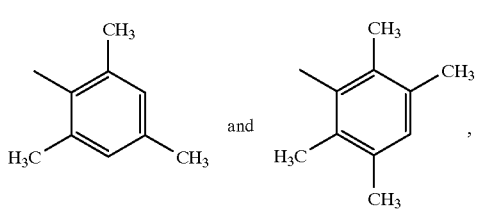

and wherein a benzoyl phthalic acid of the formula (IV)

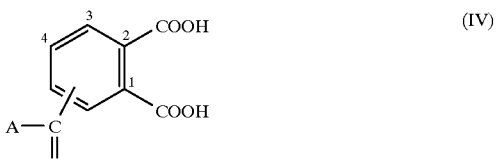

(IV)

or the mono-$C_1$–$C_4$-alkyl esters or the anhydrides thereof wherein

A has the above given meaning, is reacted with a compound of the formula (V)

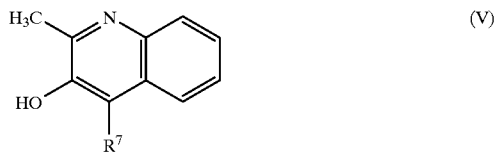

(V)

wherein $R^7$ represents H or —COOH.

This reaction is preferably carried out at a temperature of 150 to 220° C.

It is preferred to carry out this reaction in an organic solvent, like chlorobenzene, nitrobenzene, trichlorobenzene and the like.

The invention further relates to benzoyl phthalic acids of the formula (IV) and the mono-$C_1$–$C_4$ alkyl esters thereof and anhydrides thereof, wherein A is a radical selected from the group consisting of

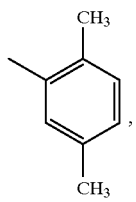 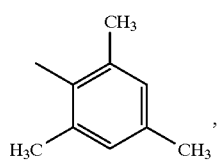

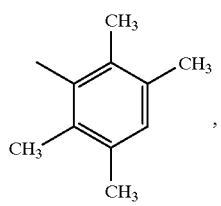 and

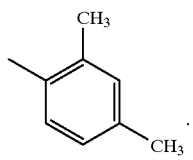

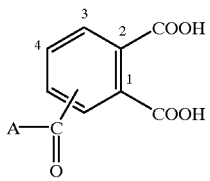

In a preferred embodiment the substituent A—CO— is connected in the 4-position of the phthalic acid ring of the formula IV.

A process for the preparation of benzoyl phthalic acid starting from trimellitic acid chloride anhydrid has already been dislosed in JP-A-425756 and U.S. Pat. No. 5,061,810, respectively. According to JP-A-425756 equivalent amounts of catalyst ($AlCl_3$, $BF_3$ or $FeCl_3$) are used. According to U.S. Pat. No. 5,061,810 superacids are used in catalytical amounts. But such a process leads to a yield of only 65%. Surprisingly, it now has been found the following process.

The invention further relates to a process for the preparation of benzoyl phthalic acids of the formula (IV)

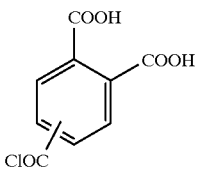

(IV)

wherein

A represents a phenyl group which is unsubstituted or substituted with one to five identical or different substituents selected from the group consisting of halogen, $C_1$–$C_4$-alkyl, $C_1$–$C_4$-alkyl-mercapto, cyano, $C_1$–$C_4$-alkyl-carbamino, $C_6$–$C_{10}$-aryl, $C_6$–$C_{10}$-aryloxy or $C_1$–$C_4$-alkoxy in which a carboxylic phthalic acid chloride of the formula (VI)

$$\text{(VI)}$$

or the anhydride thereof, preferably trimellitic acid chloride or the anhydride thereof, is reacted with the aromatic compound (VII)

A–H    (VII)

wherein A has the above mentioned broadest meaning, preferably in an inert organic solvent in the presence of $FeCl_3$ or Fe-powder in an amount of 0.001 to 0.1 moles for 1 Mol of the phthalic acid of the formula (VI) at a temperature of 60 to 180° C.

As inert organic solvent aromatic solvents can be mentioned which are not reactive as to react with the acid chloride under the reaction conditions. It is preferred to use chlorobenzene, dichlorobenzene, trichlorobenzene or nitrobenzene. But also it is preferred to use the aromatic compound VII as solvent.

After the reaction has been completed water is preferably added in order to hydrolize.

Excessive amounts of solvents preferably are removed and the benzoyl phthalic acid can be precipitated. For precipitation in addition to the water watersoluble organic solvents can be added in an amount of up to 30% by weight. This preferred embodiment leads to products having an improved purity.

As watersoluble solvents the following are mentioned: alcohols like methanol, ethanol and propanol, organic acids like formic acid, acetic acid and propionic acid, urea, dimethyl urea, tetramethyl urea, caprolactam, N-methyl pyrrolidon, dimethyl formamide and glycol ether.

Bulk dyeing here is understood as meaning, in particular, processes in which the dyestuff is incorporated into the molten plastics composition, for example with the aid of an extruder, or in which the dyestuff or dyestuff mixtures are added to the starting components for the preparation of the plastic, for example the monomers, even before the polymerization.

Particularly preferred plastics are thermoplastics, for example vinyl polymers, polyesters or polyamides.

Suitable vinyl polymers are polystyrene, styrene-acrylonitrile copolymers, styrene-butadiene copolymers, styrene-butadiene-acrylonitrile terpolymers, polymethacrylates and the like.

Polyesters which are furthermore suitable are: polyethylene terephthalates, polybutylene terephthalates, polycarbonates and cellulose esters.

Polystyrene, styrene copolymers, polycarbonates and polymethacrylate are preferred. Polystyrene is particularly preferred.

The high molecular weight compounds mentioned can be present individually or in mixtures, as plastic compositions or melts.

The dyestuffs used according to the invention are used in finely divided form, it being possible, but not necessary, for dispersing agents also to be used.

If the dyestuffs (I) are employed after polymerization of the plastic to be dyed, they are mixed or ground with the granules of the plastic in the dry state and this mixture is plasticized and homogenized, for example on mixing rolls or in extruders. However, the dyestuffs can also be added to the molten composition and they can be distributed homogeneously by stirring. The material predyed in this manner is then further processed to mouldings in the customary manner, for example by spinning to bristles, filaments and the like or by extrusion or in the injection moulding process.

Since the dyestuffs of the formula (I) are resistant to polymerization catalysts, in particular peroxides, it is also possible to add the dyestuffs to the monomeric starting materials for the plastics and then to carry out the polymerization in the presence of polymerization catalysts. For this, the dyestuffs are preferably dissolved in the monomeric components or mixed intimately with them.

The dyestuffs of the formula (I) are preferably employed for dyeing the polymers mentioned in amounts of 0.0001 to 1% by weight, in particular 0.01 to 0.5% by weight, based on the amount of polymer.

Corresponding valuable opaque dyeings can be obtained by addition of pigments which are insoluble in the polymers, such as, for example, titanium dioxide.

Titanium dioxide can be used in an amount of 0.01 to 10% by weight, preferably 0.1 to 5% by weight, based on the amount of polymer.

Transparent or opaque brilliant yellow dyeings of good heat stability and good fastness to light and weathering are obtained by the process according to the invention.

Mixtures of various dyestuffs of the formula (I) and/or mixtures of dyestuffs of the formula (I) with other dyestuffs and/or inorganic or organic pigments can also be employed in the process according to the invention.

The invention is illustrated by—but not limited to—the following examples, in which the parts are stated in terms of weight and the percentage data denote percentages by weight (wt. %).

EXAMPLE 1

A) Preparation 65 parts of hydroxyquinaldinecarboxylic acid, 200 parts of trichlorobenzene and 100 parts of 4-benzenesulphonylphthalic acid are heated at 215–220° C. for 6 hours, the water of reaction distilling off. The mixture is diluted with 200 parts of methanol and the solid is filtered off with suction and washed with methanol. Drying gives 98 parts of the dyestuff of the formula

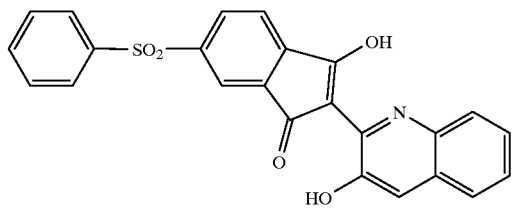

B) Dyeing examples

Example a)

100 parts of polystyrene granules and 0.02 part of the dyestuff from Example I are mixed intensively in a drum mixer for 15 minutes. The granules dyed in the dry state are processed at 240° C. on a screw injection moulding machine. Transparent yellow sheets of very good light-fastness are obtained. Instead of polystyrene polymer, it is also possible to use copolymers with butadiene and acrylonitrile. If 0.5 part of titanium dioxide is additionally added, deep opaque dyeings are obtained.

Example b)

0.015 part of the dyestuff from Example 1 and 100 parts of polymethyl methacrylate are mixed in the dry state and homogenized on a single-screw extruder at 230° C. The material emerging as a strand from the extruder is granulated. It can then be press-moulded to shapes. A plastic which has been dyed transparent yellow with good fastness to light and weathering is obtained.

Example c)

100 parts of a commercially available polycarbonate are mixed in the dry state in the form of granules with 0.03 part of the dyestuff from Example 1). The granules dusted in this way are homogenized on a twin-screw extruder at 290° C. A transparent yellow dyeing of good light-fastness is obtained. The dyed polycarbonate is discharged as a strand from the extruder and processed to granules. The granules can be processed by the customary methods for fabrication of thermoplastic compositions.

If the procedure is as described above, but with the addition of 1% of titanium dioxide, a yellow-opaque dyeing is obtained.

Example d)

0.04 part of the dyestuff is mixed in the dry state with 100 parts of styrene/acrylonitrile copolymer, the mixture is homogenized in a twin-screw extruder at 190° C. and granulated and the granules are then press-moulded to shapes in the customary manner. A transparent yellow plastic of good light-fastness is obtained.

Example e)

0.025 part of the dyestuff of Example 1) is mixed with 100 parts of polyethylene terephthalate of a transparent type and the mixture is homogenized in a twin-screw extruder at 280° C. A transparent yellow dyeing of good light-fastness is obtained. After subsequent granulation, the coloured plastic can be processed by the customary methods of thermoplastic shaping. If the procedure is carried out with the addition of 1% of titanium dioxide, an opaque dyeing is obtained.

Example f)

0.05 part of tert-dodecylmercaptan and 0.05 part of the dyestuff from Example 1 are dissolved in 98.9 parts of styrene. This solution is dispersed in a solution of 200 parts of deionized water, 0.3 part of partly hydrolysed polyvinyl acetate (for example Mowiol® 50/88 from Hoechst) and 0.05 part of dodecylbenzene-sulphonate. After addition of 0.1 part of dibenzoyl peroxide in 1 part of styrene, the dispersion is heated to 80° C., with vigorous stirring, and the polymerization is started. If the following polymerization conditions are used: 4 hours at 80° C., 2 hours at 90° C., 3 hours at 110° C., 2 hours at 130° C., the polymer is obtained in a yield of 98% of theory. The polymer is obtained in the form of beads which have a diameter of 0.1 to 1.5 mm ($D_{50}$ value), depending on the stirring conditions. The polymer is separated from the serum by filtration and dried at 110° C. to a residual moisture content of 0.5%. After melting in a mixing unit (hot roll mill), 0.5% of zinc stearate and 0.2% of Ionol® from Shell (≈2,6-di-tert-butyl-p-cresol) are admixed and the polymer is granulated.

The polymer can be processed to yellow transparent mouldings by the customary methods of thermoplastic shaping, for example in the injection moulding process.

Example g)

0.2 part of tert-dodecylmercaptan and 0.01 part of the dyestuff from Example 1) are dissolved in 74.8 parts of styrene and 25 parts of acrylonitrile, and this solution is then dispersed in a solution of 200 parts of completely deionized water and 0.2 part of a copolymer, neutralized with sodium hydroxide, of styrene and maleic anhydride. After addition of 0.1 part of dibenzoyl peroxide, dissolved in 1 part of styrene, the dispersion is heated to 80° C., with vigorous stirring, and polymerization is started. After the polymerization as in Example f), the polymer is also worked up in the same manner as described in the example. 0.5% of zinc stearate as a lubricating agent and 0.5% of Ionol® from Shell (≈2,6-di-tert-butyl-p-cresol) as an anti-ageing agent are incorporated on a hot roll mill. The granulated polymer can be injection moulded to transparent yellow mouldings.

Example h)

A solution of 99.95 parts of styrene, . . . of the dyestuff from Example 1) and 0.01 part of di-tert-butyl peroxide is introduced into a continuously operating preliminary reactor operated with an overflow, and initial polymerization is carried out at a temperature of 75° C. The initially polymerized solution emerging from the preliminary reactor (polystyrene content 20%) is introduced into a twin-screw extrusion unit. The two screws run in opposite directions at 20 revolutions per minute. The four heatable and coolable segments of the screw machine are kept at 110° C., 130° C., 160° C. and 180° C. in the sequence product intake—product discharge. The polymer leaves the screw reactor with a solids concentration of 80%. 3 parts by weight of Ionol® from Shell (≈2,6-di-tert-butyl-p-cresol) and 5 parts by weight of octyl alcohol per 1000 parts by weight of polymer solution are metered into the polymer in a subsequent extruder, and the polymer is degassed and then granulated. The granules, which have been dyed yellow, can be processed to mouldings.

Example i)

0.02 part of the dyestuff from Example 1) is dissolved in 74.97 parts of styrene and 25 parts of acrylonitrile or methacrylonitrile. After addition of 0.01 part of di-tert-butyl peroxide, the solution thus obtained is introduced into a continuously operating preliminary reactor operated with an overflow. The polymerization and working up are carried out as described in Example h). The transparent yellow granules can be further processed to profiles and sheets by the customary methods of processing thermoplastic compositions.

Example k)

0.03 part of the dyestuff from Example 1) is dissolved in 99.97 parts of methyl methacrylate. After addition of 0.1 part of dibenzoyl peroxide, the solution is heated to 120° C. and the polymerization is started. After 30 minutes, the initially polymerized methyl methacrylate is polymerized completely between two glass plates at 80° C. for 10 hours. Yellow transparent polymethyl methacrylate sheets are obtained.

Example l)

100 parts of polyamide 6 chips, obtained by polymerization of ε-caprolactam, are intimately mixed with 0.05 part of the dyestuff from Example 1 in a shaking machine. The powdered chips thus obtained are melted at 260° C. in an extruder, the resulting melt is forced through a single-hole die of 0.5 mm diameter and the emerging filament is drawn off at a rate of about 25 m/minute. The filament can be stretched four-fold in hot water. A transparent filament dyed yellow and having excellent light-fastness is obtained. If an opaque dyeing is to be obtained, 0.5 part of titanium dioxide is additionally added.

The residence time in the extruder can be up to 30 minutes without impairment of the colour shade.

The dyestuffs listed in the following Table 1, with which plastics were dyed in accordance with dyeing examples a)–l), were obtained in a manner analogous to that described in Example 1.

In these reactions, the 4-benzenesulphonylphthalic acid from Example I was laced by the phthalic acid derivatives of Table 1.

TABLE 1

| Example | Substituted derivative of phthalic acid employed | Colour shade |
|---|---|---|
| 2 | 3-Benzenesulphonyl | yellow |
| 3 | 4-(4'-Methyl-benzenesulphonyl)- | reddish-tinged yellow |
| 4 | 3-(3'-Methyl-benzenesulphonyl)- | yellow |
| 5 | 4-(2'-Methyl-benzenesulphonyl)- | reddish-tinged yellow |
| 6 | 4-(4'-t-Butyl-benzenesulphonyl)- | reddish-tinged yellow |
| 7 | 4-(2',-4'-Dimethyl-benzenesulphonyl)- | reddish-tinged yellow |
| 8 | 4-(4'-Chloro-benzenesulphonyl)- | reddish-tinged yellow |
| 9 | 4-(3'-Chloro-benzenesulphonyl)- | reddish-tinged yellow |
| 10 | 3-(2'-Chloro-benzenesulphonyl)- | yellow |
| 11 | 4-(4'-Fluoro-benzenesulphonyl)- | reddish-tinged yellow |
| 12 | 4-(4'-Bromo-benzenesulphonyl)- | reddish-tinged yellow |
| 13 | 4-(3',4'-Dichloro-benzenesulphonyl)- | reddish-tinged yellow |
| 14 | 4-(4'-Methoxy-benzenesulphonyl)- | reddish-tinged yellow |
| 15 | 3-(4'-Methoxy-benzenesulphonyl)- | yellow |
| 16 | 4-(3'-Methoxy-benzenesulphonyl)- | reddish-tinged yellow |
| 17 | 4-(4'-Ethoxy-benzenesulphonyl)- | reddish-tinged yellow |
| 18 | 4-(3'-Butoxy-benzenesulphonyl)- | reddish-tinged yellow |
| 19 | 4-(1-Naphthalenesulphonyl)- | reddish-tinged yellow |
| 20 | 4-Benzoyl- | reddish-tinged yellow |
| 21 | 3-Benzoyl- | yellow |
| 22 | 4-(4'-Methylbenzoyl)- | reddish-tinged yellow |
| 23 | 4'-(2'-Methyl-benzoyl) | reddish-tinged yellow |
| 24 | 4-(4'-Ethylbenzoyl)- | reddish-tinged yellow |
| 25 | 3-(4'-Chlorobenzoyl)- | yellow |
| 25 | 4-(3'-Chlorobenzoyl)- | reddish-tinged yellow |
| 27 | 4-(2'-Chlorobenzoyl)- | reddish-tinged yellow |
| 28 | 4-(2',4'-Dichlorobenzoyl)- | reddish-tinged yellow |
| 29 | 4-(2',5'-Dichlorobenzoyl)- | reddish-tinged yellow |
| 30 | 3-(3',4'-Dichlorobenzoyl)- | yellow |
| 31 | 4-(2',6'-Dichlorobenzoyl)- | reddish-tinged yellow |
| 32 | 3-(4'-Fluorobenzoyl)- | yellow |
| 33 | 4-(4'-t-Butylbenzoyl)- | reddish-tinged yellow |
| 34 | 4-(4'-Methoxybenzoyl)- | reddish-tinged yellow |
| 35 | 3-(2'-Methoxybenzoyl)- | yellow |
| 36 | 4-(3',4'-Dimethoxybenzoyl)- | reddish-tinged yellow |
| 37 | 4-(2'-Acetoxybenzoyl)- | reddish-tinged yellow |
| 38 | 4-(1-Naphthoyl)- | reddish-tinged yellow |
| 39 | 3-(2-Naphthoyl)- | reddish-tinged yellow |
| 40 | 4-n-Butylsulphonyl | yellow |
| 41 | 3-n-Butylsulphonyl | yellow |

Example 42 (Comparison example)

A mixture of

| | | |
|---|---|---|
| 97.9% | by weight | of commercially available polystyrene granules |
| 2% | by weight | of titanium dioxide (rutile type) and |
| 0.1% | by weight | of the dyestuff from Example 20 (dyestuff A) of the present application or of a dyestuff |

-continued

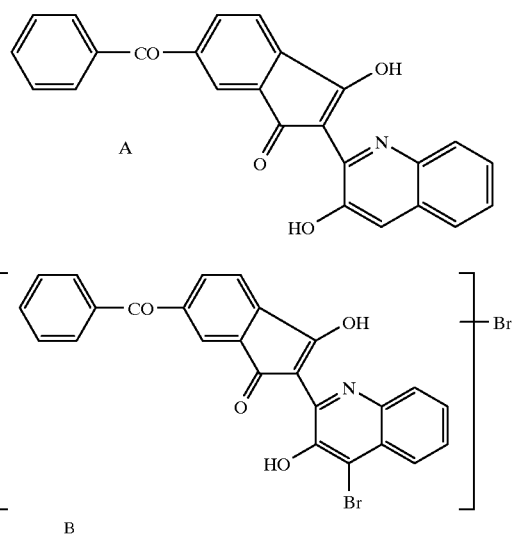

prepared according to DE 2 203 348, Example 24 (dyestuff B)

was processed to test sheets at temperatures of 220, 240, 260, 280 and 300° C. in a screw injection moulding machine with a residence time of 5 minutes.

For comparison, the same mixture is processed to the standard test sheets with the two dyestuffs at 200° C. with a residence time of 25 seconds.

For the evaluation, the test sheets are measured with the aid of spectrophotometric methods and the colour deviation from the standard is determined in the form of Δ values (see the table below).

TABLE

Differences in colour shade between the test and standard sheets

| T/° C. | Δ values dyestuff A | Δ values dyestuff B |
| --- | --- | --- |
| 220 | 0.2 | 0.0 |
| 240 | 0.3 | 0.2 |
| 260 | 0.4 | 0.9 |
| 280 | 0.6 | 2.9 |
| 300 | 0.6 | 21.5 |

In accordance with DIN 53 772, a dyestuff is regarded as heat-stable up to a Δ value of 3.

A high Δ value means a large deviation in colour shade from the standard, which in turn was produced at 220° C. in 25 seconds. This is accompanied by the heat stability at the corresponding temperature.

From the above results, it is clear that the dyestuff (A) used according to the invention surprisingly has a very much better heat stability than the previously described dyestuff (B).

Dyestuffs having good heat stabilities at high temperatures are particularly important if the processing temperatures of the plastics to be dyed are very high.

Example 43

226 g of trimellitic acid chloride anhydride were dissolved in 180 ml of o-xylene and thereto 1 of of Fe-powder were added under $N_2$-atmosphere. This solution was heated at 140° C. for 15 hours. Thereafter, the reaction solution is given onto 1000 ml of formic acid (15%). The excess of o-xylene was removed by steam distillation. It was cooled down to 25° C. and after 12 hours the reaction product was filtered off. The product was then washed with water and then dried. Yield: 276 g of 4-(4',5'-dimethylbenzoyl)-phthalic acid (92%) containing about 10% by weight of 4-(2',3'-dimethylbenzoyl)-phthalic acid. The isomers were separated by fractual cristallisation from 30% acetic acid.

Example 44

452 g of trimellitic acid chloride anhydride were dissolved in 400 ml of paraxylene. At 25° C. under $N_2$-atomosphere 1 g Fe-powder was given thereto. The solution was heated at 125° C. for 10 hours. Thereafter, the solution was given onto 1000 ml of acetic acid (15%) and the excess of xylene was removed by steam distillation.

The solution was cooled down to 25° C. and after 6 hours the reaction product was filtered off. After washing several times with water and drying 576 g of 4-(2',5'-dimethylbenzoyl)-phthalic acid (96%) were obtained.

According to example 43 and 44, respectively, the following benzoyl phthalic acids were prepared:

| Ex. 45 | 4-(2',4',6'-trimethylbenzoyl)-phthalic acid |
| Ex. 46 | 4-(2',3',5',6'-tetramethylbenzyol)-phthalic acid |
| Ex. 47 | 4-(2',6'-dimethylbenzoyl)-phthalic acid |
| Ex. 48 | 4-(2',4'-dimethylbenzoyl)-phthalic acid. |

Example 49

41 g of hydroxychinaldine carboxylic acid, 130 g of trichlorobenzene and 64 g of 4-(2',5'-dimethylbenzoyl)-phthalic acid prepared according to example 44 were heated to 220° C. for 6 hours. During the reaction the water of the reaction was removed continuously.

After cooling down to 70° C. 130 g of methanol were added. At room temperature the product was filtered off and was then washed with methanol. After drying 70 g of the dyestuff of the formula

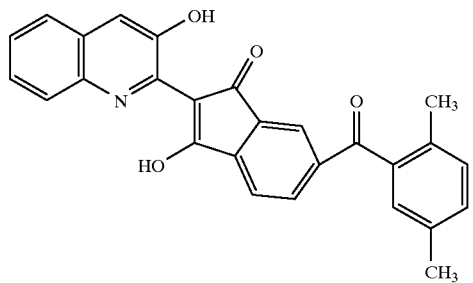

were obtained.

According to example 49 the following dyestuffs were prepared using hydroxychinaldine carboxylic acid, the phthalic derivative as listed in the following table.

TABLE

| Ex. | phthalic acid | colour shade |
| --- | --- | --- |
| 50 | 4-(2',6'-dimethylbenzoyl)phthalic acid | reddish-tinged yellow |
| 51 | 4-(2',4-dimethylbenzoyl)phthalic acid | reddish-tinged yellow |

TABLE-continued

| Ex. | phthalic acid | colour shade |
|---|---|---|
| 52 | 4-(4',5'-dimethylbenzoyl)phthalic acid | reddish-tinged yellow |
| 53 | 4-(2',3'-dimethylbenzoyl)phthalic acid | reddish-tinged yellow |
| 54 | 4-(2',4',6'-trimethylbenzoyl)phthalic acid | reddish-tinged yellow |
| 55 | 4-(2',3',5',6'-tetramethylbenzoyl)phthalic acid | reddish-tinged yellow |

The dyestuffs of examples 49 to 55 were used to dye plastics in accordance with dyeing example a)–l).

I claim:

1. A benzoyl phthalic acid of the formula (IV)

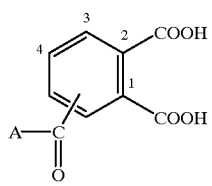

(IV)

and the mono-$C_1$–$C_4$-alkyl esters thereof and the anhydrides thereof wherein A is a radical selected from the group consisting of

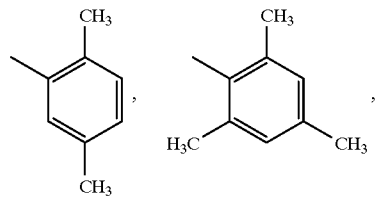

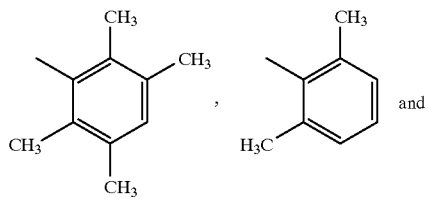

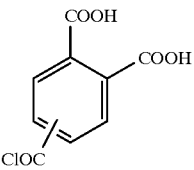

2. A benzoyl phthalic acids according to claim 1 wherein the substituent A—CO— is connected in the 4-position of the phthalic acid ring of the formula (IV).

3. A process for the preparation of benzoyl phthalic acids according to claim 1 in which a carboxylic phtalic acid chloride of the formula (VI)

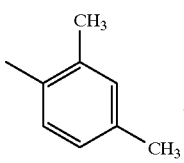

(VI)

or the anhydride thereof, is reacted with an aromatic compound (VII)

A–H    (VII)

in an inert organic solvent in the presence of $FeCl_3$ or Fe-powder in an amount of 0.001 to 0.1 moles for 1 Mol of the phthalic acid of the formula (VI) at a temperature of 60 to 180° C.

* * * * *